United States Patent
Lee et al.

(10) Patent No.: US 7,046,834 B2
(45) Date of Patent: May 16, 2006

(54) METHOD FOR MEASURING BONE MINERAL DENSITY BY USING X-RAY IMAGE

(75) Inventors: Sooyeul Lee, Taejon (KR); Seunghwan Kim, Taejon (KR); Ji-Wook Jeong, Daegu (KR); Seon Hee Park, Taejon (KR)

(73) Assignee: Electronics and Telecommunications Research Institute (KR)

( * ) Notice: Subject to any disclaimer, the term of this patent is extended or adjusted under 35 U.S.C. 154(b) by 700 days.

(21) Appl. No.: 10/029,103

(22) Filed: Dec. 21, 2001

(65) Prior Publication Data
US 2002/0181755 A1 Dec. 5, 2002

(30) Foreign Application Priority Data
May 9, 2001 (KR) .............................. 2001-25238
Jul. 26, 2001 (KR) .............................. 2001-45123

(51) Int. Cl.
*G01K 9/00* (2006.01)
*G01N 23/04* (2006.01)
*G01T 1/36* (2006.01)
*G01B 15/02* (2006.01)

(52) U.S. Cl. ..................... 382/132; 378/62; 378/83; 378/89

(58) Field of Classification Search ............... 382/132, 382/130; 378/62, 83, 87, 88, 89
See application file for complete search history.

(56) References Cited

U.S. PATENT DOCUMENTS

| | | | | |
|---|---|---|---|---|
| 5,335,260 | A | 8/1994 | Arnold | 378/207 |
| 5,602,935 | A * | 2/1997 | Yoshida et al. | 382/132 |
| 5,633,511 | A * | 5/1997 | Lee et al. | 250/587 |
| 5,712,892 | A | 1/1998 | Weil et al. | 378/54 |
| 6,064,716 | A | 5/2000 | Siffert et al. | 378/53 |
| 6,205,348 | B1 * | 3/2001 | Giger et al. | 600/407 |
| 6,324,252 | B1 * | 11/2001 | Siffert et al. | 378/56 |
| 6,370,265 | B1 * | 4/2002 | Bell et al. | 382/132 |
| 6,671,394 | B1 * | 12/2003 | Sako | 382/132 |
| 6,763,257 | B1 * | 7/2004 | Rosholm et al. | 600/407 |
| 2002/0196966 | A1 * | 12/2002 | Jiang et al. | 382/132 |

FOREIGN PATENT DOCUMENTS
KR 1020010055220 7/2001

* cited by examiner

*Primary Examiner*—Jingge Wu
*Assistant Examiner*—Anthony Mackowey
(74) *Attorney, Agent, or Firm*—Blakely Sokoloff Taylor & Zafman

(57) ABSTRACT

A method for measuring a bone mineral density, by use of an x-ray image, in a bone mineral density measuring system, includes the steps of: (a) obtaining an X-ray image of bone; (b) setting a region of interest on the obtained X-ray image of bone; (c) calculating a background trend due to soft tissues, at a bone portion within the selected region of interest; and (d) calculating an index of the bone mineral density by removing the background trend due to the soft tissues, at the bone portion within the selected region of interest.

12 Claims, 8 Drawing Sheets

METHOD FOR MEASURING BONE MINERAL DENSITY BY USING X-RAY IMAGE

FIELD OF THE INVENTION

The present invention relates to a method for measuring a bone mineral density using an X-ray image. More particularly, the present invention relates to a method for measuring a bone mineral density by removing an X-ray absorption effect due to soft tissues contained in a bone portion of an X-ray image, when the bone mineral density is measured using the X-ray image, and a storage medium being readable on a computer storing a program to implement the method.

DESCRIPTION OF THE PRIOR ART

Osteoporosis is a wide spread medical condition that affects the middle-aged and older populations. Especially, the condition is prevalent in postmenopausal women. Osteoporosis is characterized by an abnormal loss in bone mineral content, which leads to a tendency toward non-traumatic bone fractures and to structural deformations of bones. However, effective therapy for osteoporosis has not been developed yet. Accordingly, it is important that a method for easily and inexpensively diagnosing the osteoporosis should be developed for the prevention of deterioration of osteoporosis and early stage treatment of osteoporosis.

Bone mineral density is one of important factors for diagnosing osteoporosis. Various bone mineral density measurement methods have been developed.

Quantitative computed tomography (QCT) provides a three-dimensional bone density image and thus provides separate estimations of cortical and trabecular bone densities. Based on the three-dimensional bone density image, QCT method can provides a structural stability of a bone to some extent. However, there are some limitations to use the QCT as a routine screening tool for osteoporosis because the price of the QCT equipment is very high and the radiation dose of a QCT scan is generally several hundred times larger than that of a plain x-ray imaging.

The most widely used method for measuring bone mineral density and for follow-up study of osteoporosis patients is a dual energy x-ray absorptiometry (DEXA). The precision error of the DEXA in determining bone mineral density is reported to be about few percents. Furthermore, the radiation dose of a DEXA scan is very small compared with a QCT scan.

Broadband ultrasound absorption (BUA) is also used for measuring bone mineral density. However, BUA is not so accurate in determining bone mineral density compared with other equipments. Nevertheless the validity of BUA for osteoporosis study does not diminish because recent studies have reported that BUA is somewhat relevant to the mechanical strength of bone.

In spite of the various methods prescribed above, such as QCT, DEXA, and BUA, methods for measuring bone mineral density and diagnosing osteoporosis by using an x-ray image are developed steadily in the practical point of view. The reason is that most hospitals are equipped with an x-ray imaging system basically, so there is no need for an extra cost to purchase a new bone mineral density measuring system. Moreover, the high quality of an x-ray image enables trabecular pattern analysis. Particularly, it is believed that the trabecular pattern contains useful information about the fracture risk due to osteoporosis. In this sense, many researchers study trabecular patterns to extract useful information related to the fracture risk.

Up to now, various methods for measuring bone mineral density by using an x-ray image have been developed. However, bone image in the X-ray image contain significant amount of x-ray absorption effects due to overlapping soft tissues. Actually, in the anterior-posterior x-ray image of a femoral neck, the amount of x-ray absorption due to overlapping soft tissues is comparable to the amount of x-ray absorption due to the femoral neck itself. By the way, x-ray absorption due to overlapping soft tissues can not be easily removed in the simple x-ray imaging scheme, which leads to a relatively low accuracy in the bone mineral density measured by using an x-ray image.

SUMMARY OF THE INVENTION

It is, therefore, an object of the present invention to provide a method for measuring a bone mineral density by removing an X-ray absorption effect due to soft tissues contained in a bone portion of an x-ray image, when the bone mineral density is measured using the X-ray image, and a storage medium being readable on a computer storing a program to implement the method.

In accordance with an aspect of the present invention, there is provided a method for measuring a bone mineral density, by use of an x-ray image, in a bone mineral density measuring system, comprising the steps of: (a) obtaining an X-ray image of a bone; (b) setting a region of interest on the obtained X-ray image of bone; (c) calculating a background trend due to soft tissues, at a bone portion within the set region of interest; and (d) calculating an index of the bone mineral density by removing the background trend due to the soft tissues, at the bone portion within the set region of interest.

In accordance with another aspect of the present invention, there is provided a storage medium being readable on a computer storing a program to implement a method for measuring a bone mineral density, by use of an x-ray image, in a bone mineral density measuring system, comprising the steps of: (a) obtaining an X-ray image of a bone; (b) setting a region of interest on the obtained X-ray image of bone; (c) calculating a background trend due to soft tissues, at a bone portion within the set region of interest; and (d) calculating an index of the bone mineral density by removing the background trend due to the soft tissues, at the bone portion within the set region of interest.

BRIEF DESCRIPTION OF THE DRAWINGS

The above and other objects and features of the present invention will become apparent from the following description of preferred embodiments taken in conjunction with the accompanying drawings, in which.

DETAILED DESCRIPTION OF THE INVENTION

Figure 1:
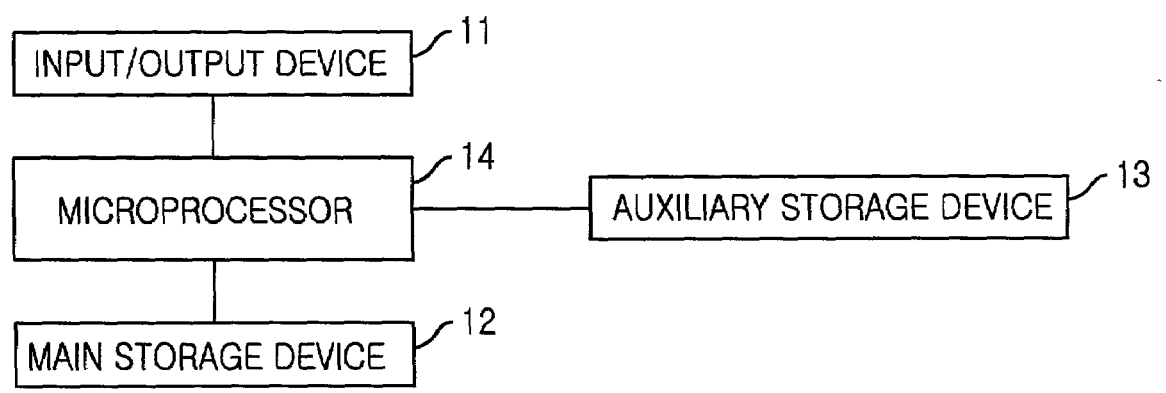
FIG. 1 shows a bone mineral density measuring system to which the present invention is applied.

Referring to FIG. 1, there is shown an exemplary diagram illustrating a bone mineral density measuring system for measuring a bone mineral density in accordance with the present invention.

As shown, the system for measuring a bone mineral density includes an input/output device 11 for inputting or outputting data required for measuring the bone mineral density by a user, main/auxiliary storage devices 12 and 13 for storing various data necessary for a process of measuring the bone mineral density by using an x-ray image, and a microprocessor 14 for controlling the input/output device 11 and the main/auxiliary storage devices 12 and 13 and controlling full operations for measuring the bone mineral density by using an x-ray image.

The input/output device 11 includes a monitor, a printer, and an x-ray film scanner for digitizing an x-ray film. If a digital image sensor (CCD or CMOS sensor) is used instead of an x-ray film, the digital image sensor is included in the input/output device 11.

Through the above system, the method for measuring the bone mineral density by using the x-ray image is carried out in accordance with the following procedures. At first, the x-ray image is inputted into the input/output device 11 with a program including a process of the following FIGS. 2A to 2C incorporated in the microprocessor 14. When the program is executed, the bone mineral density is measured by using the x-ray image according to the program.

The process is described in greater detail hereinafter with reference to FIGS. 2A to 7.

Figure 2A:
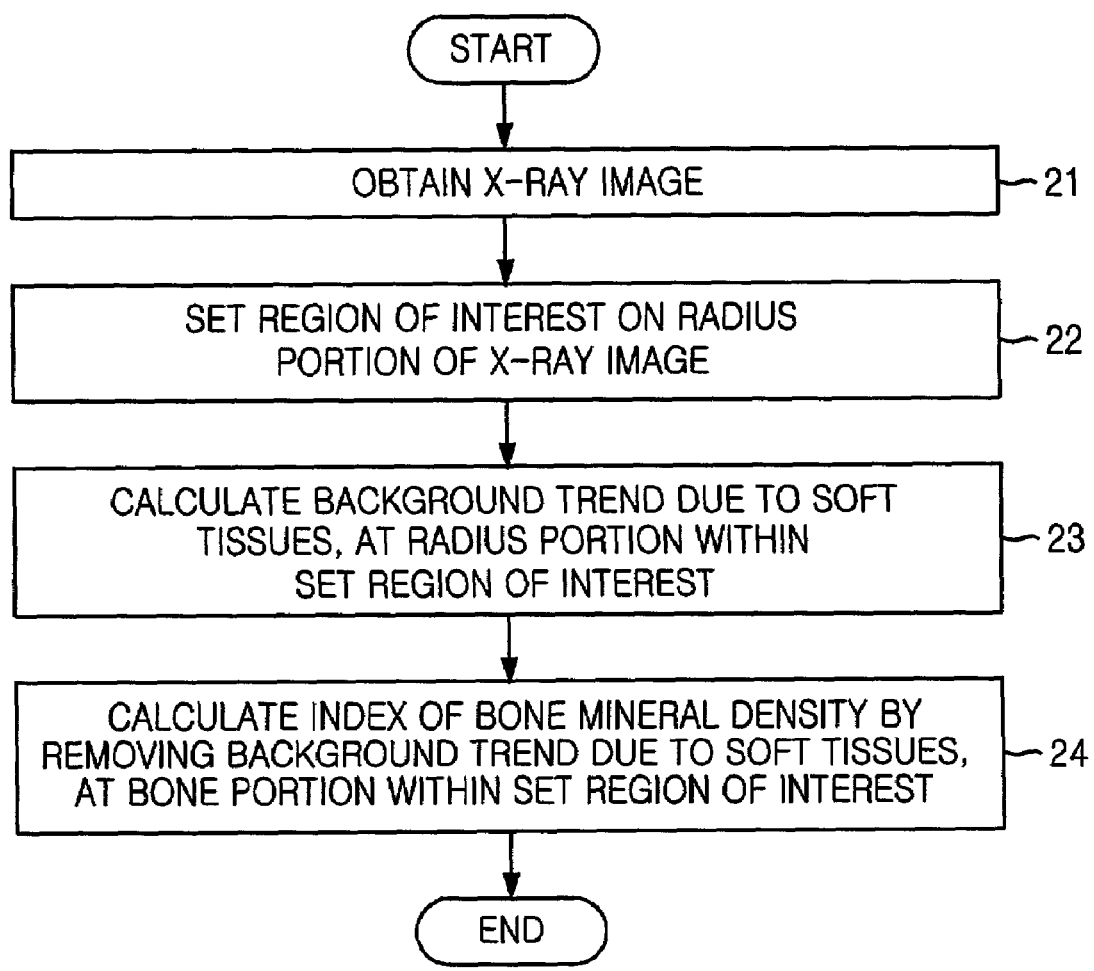
FIG. 2A is a flowchart illustrating a method for measuring a bone mineral density using an X-ray image in accordance with an embodiment of the present invention.
Figure 2B:
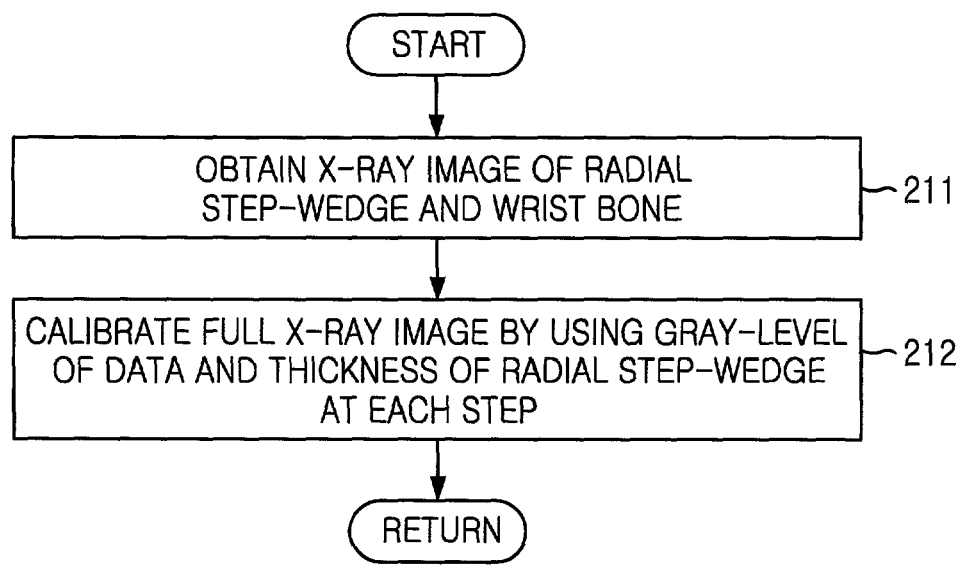
FIG. 2B is a detailed exemplary flowchart describing a step for obtaining the X-ray image shown in FIG. 2A.
Figure 2C:
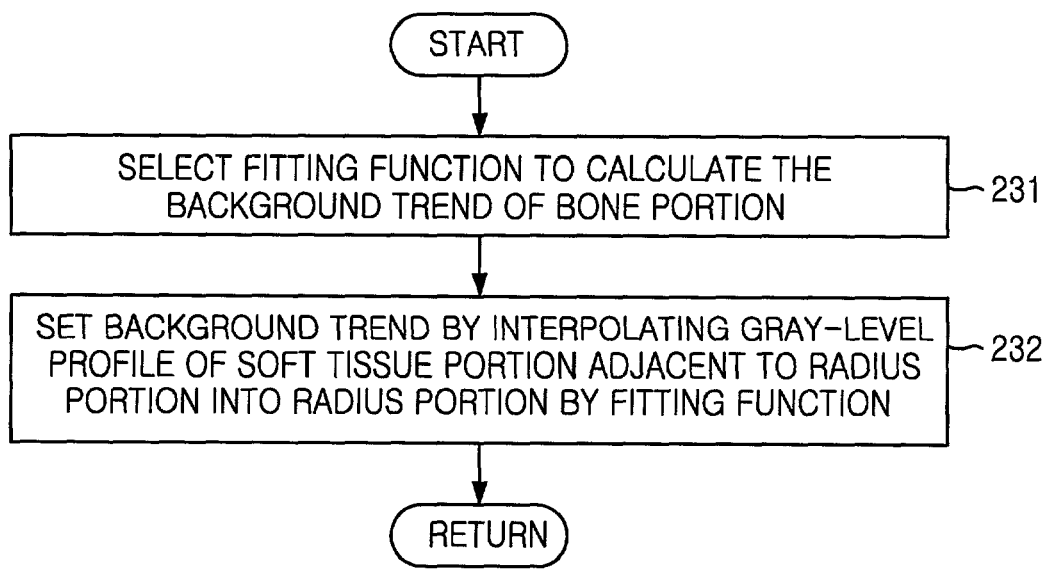
FIG. 2C is a detailed exemplary flowchart describing a step for calculating a background trend due to soft tissues within a radius portion in a region of interest shown in FIG. 2A.

FIG. 2A is a flowchart illustrating a method for measuring bone mineral density by using an x-ray image in accordance with the present invention. FIG. 2B is a detailed exemplary flowchart showing a process for obtaining the x-ray image according to the present invention. FIG. 2C is a detailed exemplary flowchart showing a process for calculating a background trend due to soft tissues within a radius portion in a region of interest.

Figure 3:
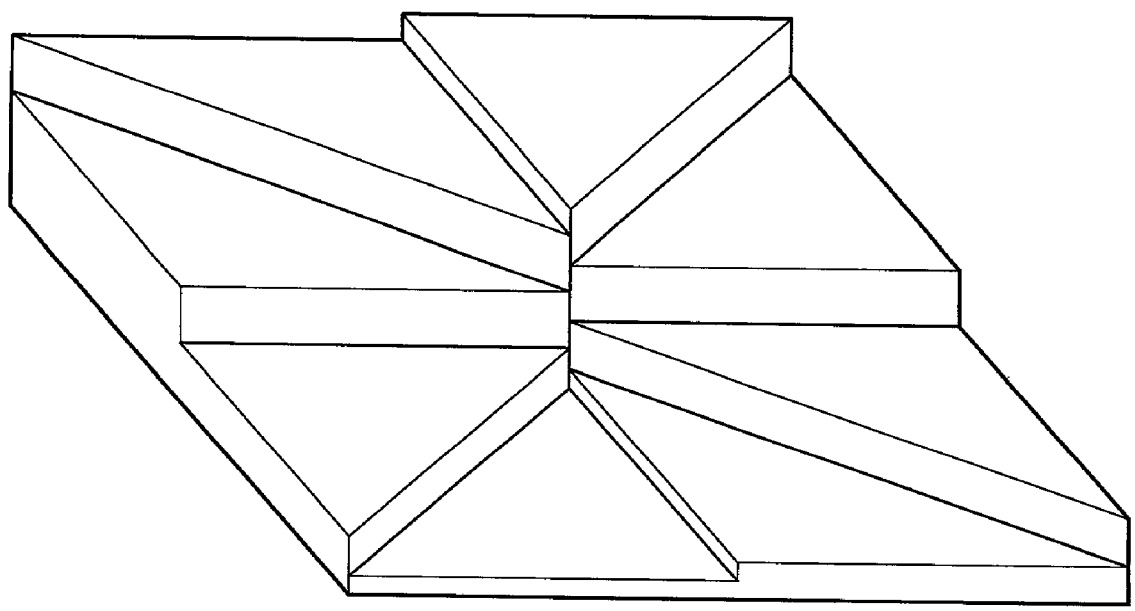
FIG. 3 is an exemplary view showing an aluminum step-wedge used to calibrate the X-ray image in accordance with the present invention.

FIG. 3 is an exemplary view illustrating an aluminum step-wedge, which is utilized to calibrate the x-ray image, in accordance with the present invention. The aluminum step-wedge is utilized to adjust the variation of the image characteristics dependent on the x-ray generation unit, the types of a screen or a film, the development condition of the film, and the characteristics of an x-ray film digitizer (the characteristics of the CCD or CMOS sensor, in case of a digital image sensor).

Figure 4:
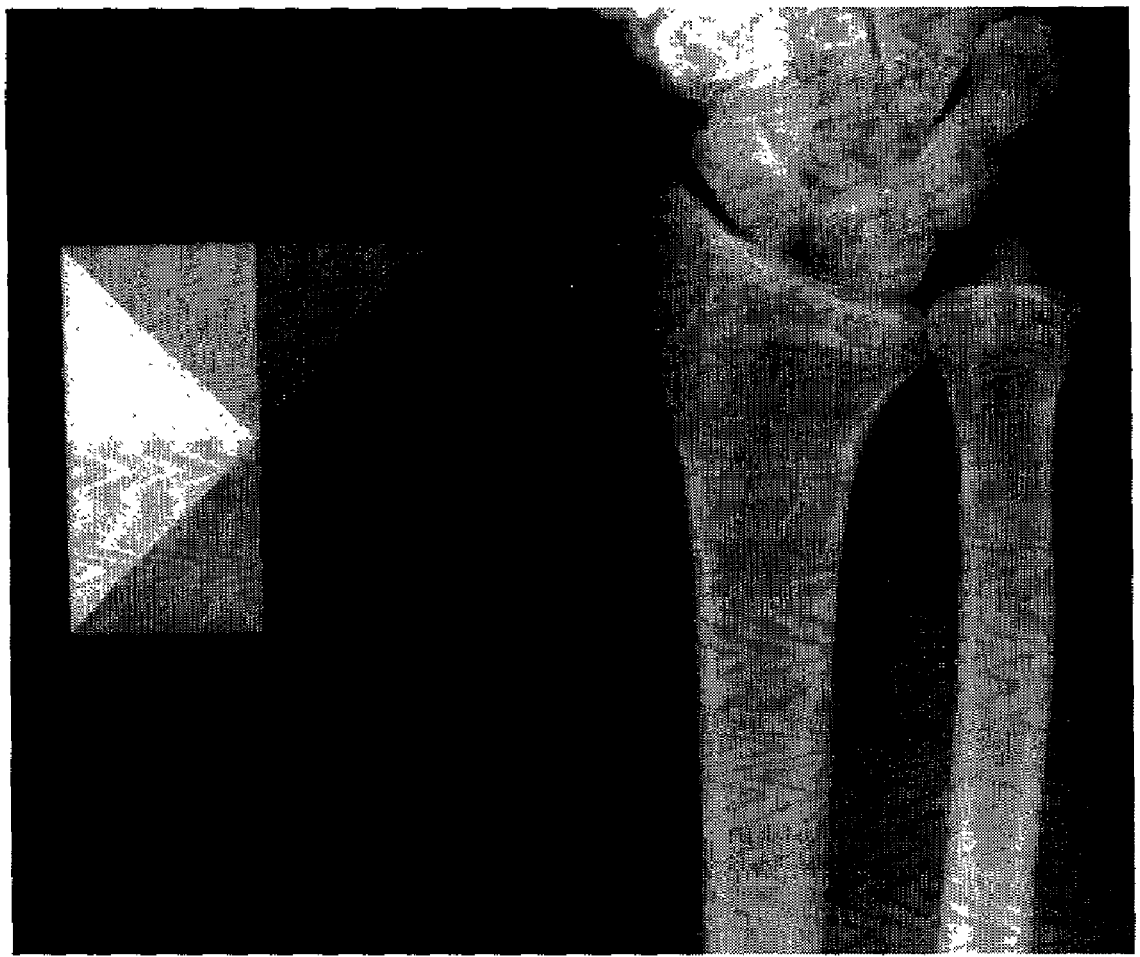
FIG. 4 is an exemplary view of the X-ray image obtained after imaging a step-wedge and a wrist together in accordance with the present invention.
Figure 5:
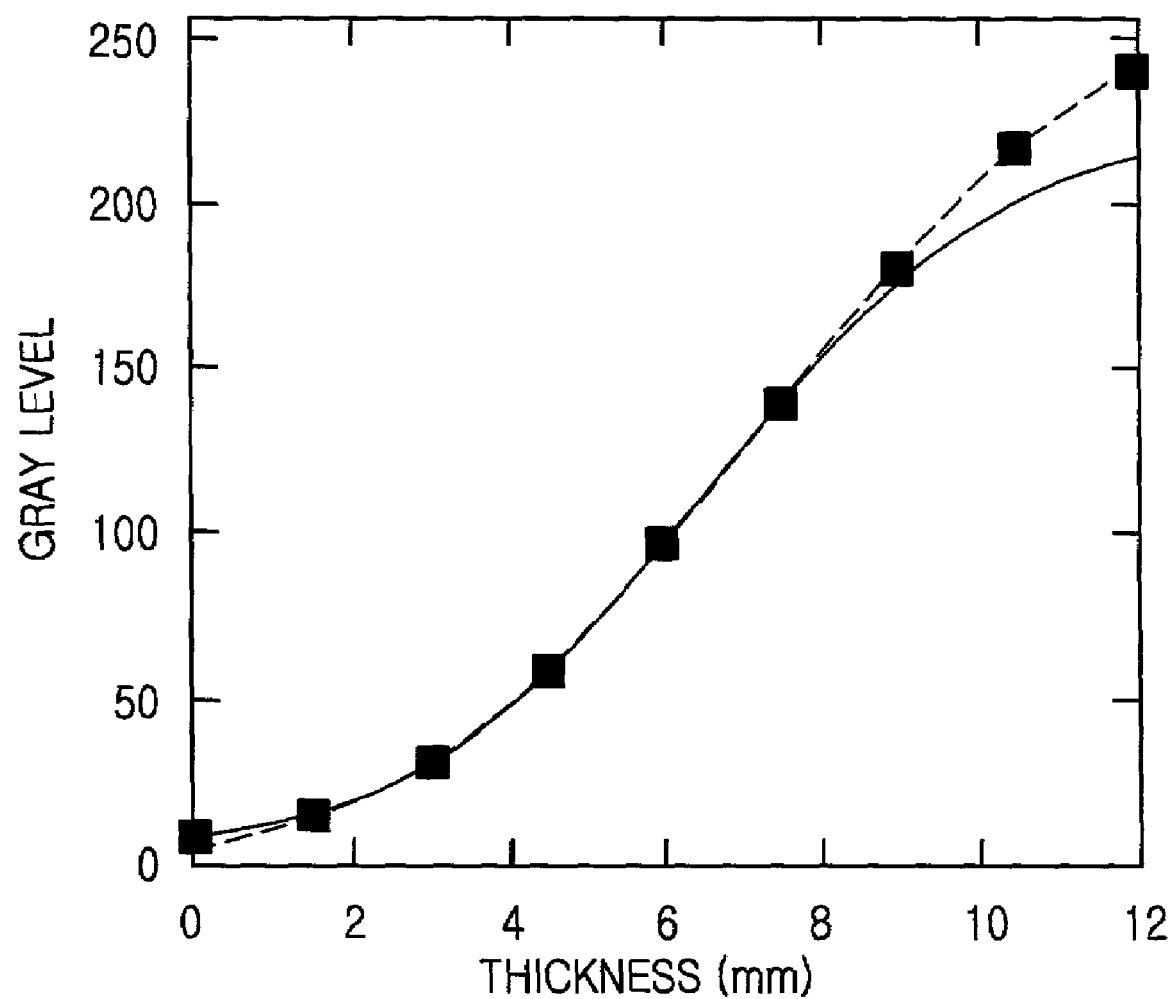
FIG. 5 illustrates an exemplary relationship between the thickness of the step-wedge and the average gray-level of the step-wedge shown in FIG. 4.
Figure 6A:
FIG. 6A illustrates the X-ray image calibrated by the step-wedge and a rectangular region of interest selected to measure the bone mineral density of a radius bone in accordance with the present invention.
Figure 6B:
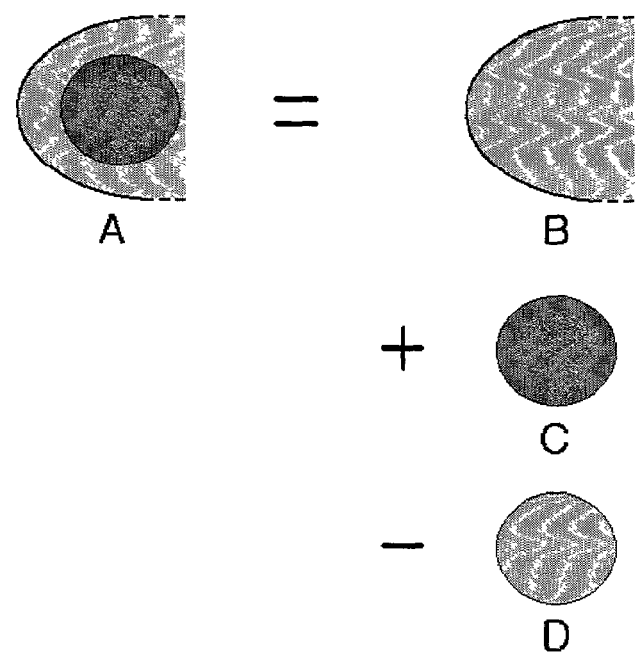
FIG. 6B illustrates a wrist cross-sectional view taken along a horizontal line 1 of the region of interest.
Figure 7A:
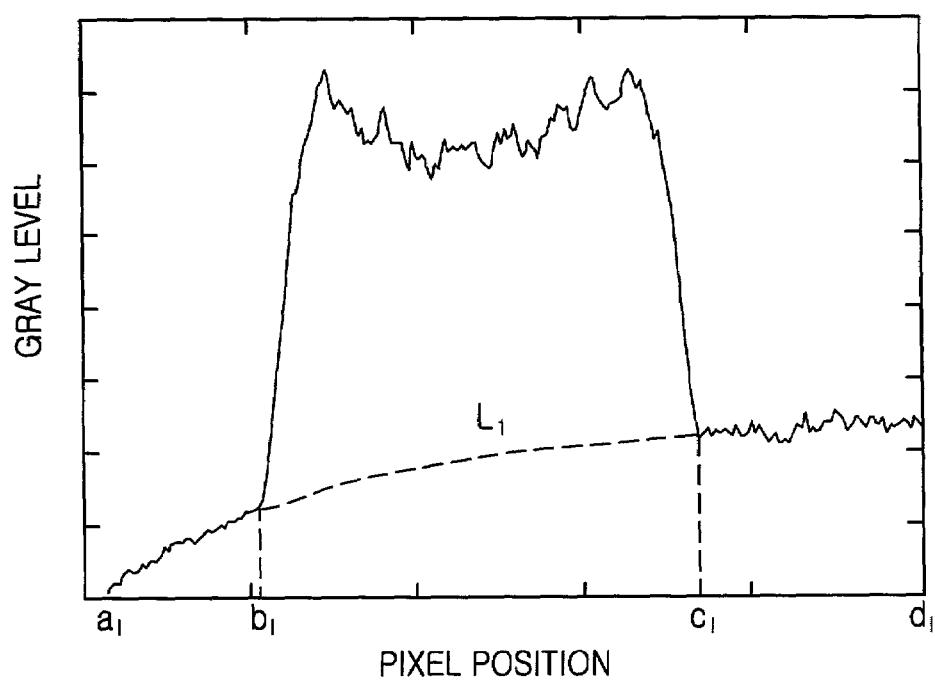
FIG. 7A illustrates a gray-level profile taken along the horizontal line 1 shown in FIG. 6A.
Figure 7B:
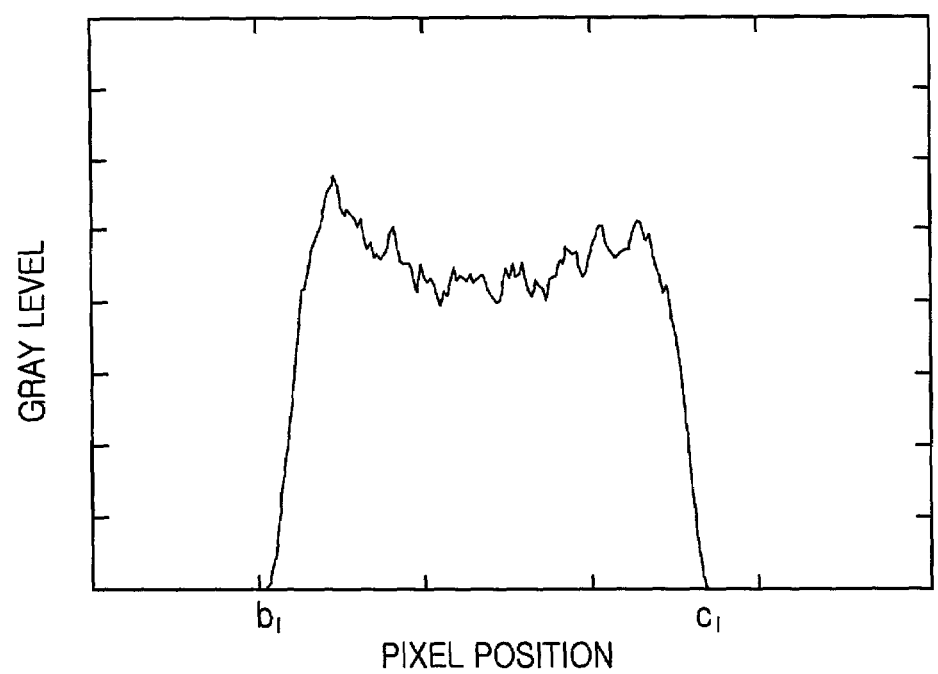
FIG. 7B illustrates a gray-level profile along the horizontal line 1 after the background trend due to the overlapping soft tissues in the radius portion is removed.

FIG. 4 is an exemplary view of the X-ray image obtained after imaging a step-wedge and a wrist together in accordance with the present invention. FIG. 5 illustrates an exemplary relationship between the thickness of the step-wedge and the average gray-level of the step-wedge shown in FIG. 4. FIG. 6A illustrates the X-ray image calibrated by the step-wedge and a rectangular region of interest selected to measure the bone mineral density of a radius bone in accordance with the present invention. FIG. 6B illustrates a wrist cross-sectional view taken along a horizontal line 1 of the region of interest. FIG. 7A illustrates a gray-level profile taken along the horizontal line 1 shown in FIG. 6A. FIG. 7B illustrates a gray-level profile along the horizontal line 1 after the background trend due to the soft tissues is removed.

At first, as shown in FIG. 2A, the x-ray image of a wrist is obtained to measure the bone mineral density in accordance with the present invention (step 21). When the x-ray image is obtained, the conditions for obtaining the x-ray image shall be kept constant as possible. In particular, a tube voltage (kVp) and a tube current (mA) of an x-ray generation unit should be fixed to specific values. For example, when the x-ray image of the wrist described above is obtained, the tube voltage and the tube current of the x-ray generation unit shall be 50 kVp and 50 mA, respectively. The x-ray image is obtained by digitalizing an x-ray film, which was obtained by a simple x-ray imaging process, using an x-ray film scanner. When a digital image sensor is used, the x-ray image is obtained directly without a step of using the film scanner. When the x-ray image is obtained, its spatial resolution shall be 200 PPI (pixels per inch) and each pixel shall be of an 8-bit gray level.

FIG. 4 is an exemplary view of an x-ray image of a wrist, which is obtained by digitalizing an x-ray film. Each pixel of the x-ray image consists of a gray-level associated with the amount of x-ray absorption by the body. The amount of x-ray absorption is determined by a density or thickness of bone and soft tissues. Generally, the x-ray image of bone also includes x-ray absorption effects due to overlapping soft tissues. Accordingly, to accurately measure bone mineral density using the x-ray image, it is necessary to remove x-ray absorption effects due to the overlapping soft tissues from the x-ray image.

In the meantime, the characteristics of the x-ray image, such as brightness, contrast, etc. are sensitive to the change of x-ray imaging conditions. In other words, the brightness, i.e. gray-level, of the x-ray image at each pixel cannot be an absolute measure for the amount of x-ray absorption. Therefore, when the bone mineral density is measured by using the x-ray image, it is necessary to calibrate a variation of image characteristics due to the change of the x-ray imaging conditions and to quantify the amount of x-ray absorption at each pixel.

In order to calibrate the variation of characteristics of the x-ray image due to x-ray imaging conditions, and quantify the amount of x-ray absorption at each pixel, a metallic step-wedge composed of several steps is used as shown in FIG. 3. Aluminum or copper is suitable for a material of the step-wedge. Generally, the material and thickness of the step-wedge are properly selected according to a body portion where the bone mineral density is measured. Conventionally, the material and thickness are selected in such a way that the amount of x-ray absorption by the highest step of the step-wedge is slightly larger than the maximum amount of x-ray absorption by the body portion where bone mineral density is to be measured. When the bone mineral density is measured at the wrist, the appropriate maximum thickness of the aluminum step-wedge is 12 mm. For a step-wedge containing heavy metals such as copper, etc., the maximum thickness shall be reduced in consideration that the x-ray absorption becomes larger. The step-wedge shown in FIG. 3 is made of an aluminum plate of which a bottom surface is a square with a dimension of 40 mm×40 mm and thickness is 12 mm, processed into radial steps having eight steps. In the aluminum step-wedge described above, the heights of steps are 1.5, 3.0, 4.5, 6.0, 7.5, 9.0, 10.5 and 12.0 mm, in an increasing order.

As shown in FIG. 2B, in order to calibrate a characteristic variation of the x-ray image due to the x-ray imaging conditions, and to quantify the amount of x-ray absorption at each pixel, an x-ray image of the radial step-wedge and a wrist is obtained (step 211). FIG. 4 is an exemplary view of the x-ray image where the step-wedge and the wrist are imaged together. In FIG. 5, two-dimensional data between the thickness of the step-wedge and the average gray-level of the step-wedge shown in FIG. 4 are denoted by solid squares. In FIG. 5, the average gray-level, when the thickness of the step-wedge is zero, corresponds to the average of background gray-levels around the step-wedge.

Then, as shown in FIG. 2B, the full x-ray image is calibrated by using above two-dimensional data between the thickness of the step-wedge and the average gray-level of the step-wedge (step 212). In order to calibrate the full x-ray image by using the two-dimensional data, average gray-level at any thickness of the step-wedge should be calculated. In order to calculate the average gray-level at any thickness of the step-wedge, the two-dimensional data shown in FIG. 5 are fitted to an appropriate function. In FIG. 5, the gradient of the average gray-level increases gradually at first and then decreases gradually as the thickness of the step-wedge increases. One of the functions with the characteristics described above is a tangent hyperbolic function. Thus a fitting function of "$f(t)=a+b*\tanh(c*t+d)$" is used, where "$f(t)$" represents the gray-level, "$t$" represents the thickness (mm) of the step-wedge, and "$a$", "$b$", "$c$" and "$d$" represent the fitting parameters, respectively. Here, the function "$f(t)$" is symmetric with respect to a point of "$t=-d/c$". However, as shown in FIG. 5, the gray level profile of the step-wedge is not completely symmetric. Thus a fitting of data in FIG. 5 to a single fitting function "$f(t)$" may create considerable fitting errors. Accordingly, in the present invention, the data are divided into two parts and then data of each part are fitted to the function "$f(t)$". The fitting function "$f(t)$" has four fitting parameters, so there needs to have more than four data in each fitting part. The first part consists of six data with heights of 0 mm to 7.5 mm. The second part consists of six data with heights of 4.5 mm to 12.0 mm. Here, the overlap of the two parts is to softly couple fitting results. The fitting is carried out in each part. The Levenberg-Marquardt fitting method is used as a fitting method in the present invention.

Here, "$f_1(t)$" denotes the fitting result in the first part, and "$f_2(t)$" denotes the fitting result in the second part, and the results are shown in FIG. 5 as a solid line and a dotted line, respectively. Then, the two fitting functions are coupled together to provide a final fitting function "$F(t)$" as follows. At first, "$F(t)=f_1(t)$" for "$t<=4.5$", "$F(t)=f_2(t)$" for "$t>=7.5$", and "$F(t)=f_1(t)+(1-x)f_2(t)$" for "$4.5<t<7.5$". Here $x=(7.5-t)/3$. The function "$F(t)$" is a simply increasing function, so the inverse function $F^{-1}(g)$ is well defined. Here "$g$" denotes the gray-level. Now, the gray-level "$g$" of each pixel of the x-ray image is calibrated as following procedures by using the final fitting function "$F(t)$". In case of "$g>=F(12)$", the calibrated gray-level is "255". In case of "$g<=F(0)$", the calibrated gray-level is 0. In other case, the calibrated gray-level is an integer part of "$256*F^{-1}(g)/12$".

FIG. 6A shows a calibrated image of FIG. 4, which was obtained via the calibration method described above.

Then, as shown in FIG. 6A, in order to remove the X-ray absorption effect due to soft tissues contained in the radius portion of the X-ray image, a rectangular region of interest is set on the radius portion (step 22). A size of the region of interest is 250×150 pixels, and the region of interest should contain soft tissue regions to the left and right sides of the radius.

Then, the background trend due to soft tissues is calculated within the radius portion in the region of interest (step 23).

In order to help the understanding of the method for calculating the background trend due to soft tissues, a wrist cross-section "A" along a crossing line 1 of FIG. 6A is shown schematically in FIG. 6B. An inner dark portion in the cross-section "A" is a radius portion and an outer bright portion is a soft tissue portion. Generally, the cross-section of a long bone such as a radius bone is approximately a disc shape. Accordingly, the cross-section of the radius bone is simplified as a disc shape hereinafter. As shown in FIG. 6B, the cross-section "A" is decomposed as follows: (cross-section "A")=(cross-section "B")+(cross-section "C")−(cross-section "D"), where the cross-section "B" is equal to the cross-section "A" except that the radius bone is replaced with soft tissues, the cross-section "C" is equal to the bone portion in the cross-section "A", and the cross-section "D" is equal to the cross-section "C" except that the radius bone is replaced with soft tissues. On the other hand, the gray-level profile along the line 1 in FIG. 6A is drawn by a solid line in FIG. 7A. In FIG. 7A, the horizontal axis denotes a coordinate of pixel and the vertical axis denotes a gray-level. In FIG. 7A, intervals "$a_l$–$b_l$", "$b_l$–$c_l$" and "$c_l$–$d_l$" are a soft tissue region, a radius bone region, and another soft tissue region, respectively.

In the interval "$b_l$–$c_l$" of FIG. 7A, it is impossible to exactly calculate the background gray-level trend due to soft tissues from the simple x-ray imaging scheme. Accordingly, an approximate method is introduced to calculate the background trend. In the present invention, we use an interpolation method where gray-level profiles of the two soft tissue regions "$a_l$–$b_l$" and "$c_l$–$d_l$" are interpolated into the radius region "$b_l$–$c_l$" to set it to a background trend. For the sake of interpolation, a differentiable fitting function is selected (step 231). Generally, a polynomial function is suitable for the fit. However, in the present invention, only a $4^{th}$ order polynomial is used for the fit. The interpolation is accomplished by fitting data of the soft tissue regions "$a_l$–$b_l$" and "$c_l$–$d_l$" into the $4^{th}$ order fitting function through a Levenberg-Marquardt fitting method. The interpolation result in the radius bone region is set to the background trend due to soft tissues. That is, the gray-level profiles of the soft tissue regions adjacent to the radius region are interpolated into the radius region using the chosen fitting function to set the background trend (step 232). Seeing this method in detail, the method includes a step of obtaining the gray-level profile across the radius bone in the region of interest, a step of dividing the gray-level profile into the bone portion and the soft tissue portions, and a step of interpolating the gray-level profiles of the soft tissue portions into the bone portion with the fitting function to set the fitting result to the background trend due to the soft tissues in the bone region. "L1" of FIG. 7A is the background trend interpolated via the above method. This background trend corresponds to the gray-level profile due to the cross-section "B" of the FIG. 6B. Now, the background trend is calculated with the cross-sectional line 1 moved to all the rows.

If the background trend has been set, the background trend due to the soft tissues is removed from gray levels of the radius region to calculate an index for the bone mineral density (step 24). The step 24 includes a step of removing the background trend in the gray level of each pixel of the bone region, a step of calculating an average gray level ($<G>$) in the bone region after removing the background trend, a step of calculating a weighted average (P) of radius bone widths within the region of interest, and a step of establishing an index for the bone mineral density as $<G>+c_0P$. Here, $c_0$ is an unknown constant that should be determined.

FIG. 7B shows the gray-level profile after removing the background trend in the radius region "$b_I$–$c_I$". The gray-level profile of FIG. 7B may be approximately the same as the gray-level profile due to the cross-section "C" in FIG. 6B after removing the gray-level profile due to the cross-section "D". The bone mineral content of the radius bone is determined by a sum of the gray-level profiles due to the cross-section "C" in FIG. 6B. Thus, in the radius portion "$b_I$–$c_I$", the sum ($G_I^{(C)}$) of the gray-level profile due to the cross-section "C" is obtained by adding a sum of the gray-level profile due to the cross-section "D" to a sum of the gray-level profile of FIG. 7B.

$$G_I^{(C)} = \sum_{n=b_1}^{c_1} [G_{In} + G_{In}^{(D)}] \quad \text{Eq. 1}$$

In Eq. 1, "$G_{In}$" denotes the gray-level profile in FIG. 7B, "$G_{In}^{(D)}$" denotes the gray-level profile due to the cross-section "D", and "n" denotes an index for pixel. In order to calculate "$G_{In}^{(D)}$", the gray-level profile due to the cross-section "D" should be known and in order to know this gray-level profile the shape of the cross-section "D" should be known. However, it is impossible to know an exact shape of the cross-section "D" from the X-ray image. Accordingly, the cross-section "D" of the radius bone is approximated to a disc based on the fact that it is anatomically close to the disc and a diameter of the disc is defined as $p_I=|c_I-b_I|$. Then, "$G_I^{(C)}$" is approximately equal to Eq. 2.

$$G_I^{(C)} = \sum_{n=b_1}^{c_1} G_{In} + c_0 p_1^2 \quad \text{Eq. 2}$$

In Eq. 2, "$c_0$" is a constant.

Now, after calculating Eq. 2 with respect to all the cross-sectional lines within the region of interest, the sum of all the $G_I^{(C)}$ is given by the following Eq. 3.

$$\sum_1 G_I^{(C)} = \sum_1 \sum_{n=b_1}^{c_1} G_{In} + c_0 \sum_1 p_1^2 \quad \text{Eq. 3}$$

The left-hand side of Eq. 3 is an index for total radius bone mineral content within the region of interest.

Now, the left and right-hand sides of Eq. 3 are divided by the area of the radius bone $$A \equiv \sum_1 p_1$$

within the region of interest, and the obtained value is determined as the index for the radius bone mineral density ($G^{(C)}$).

$$G^{(C)} = \frac{1}{A} \sum_1 \sum_{n=b_1}^{c_1} G_{In} + \frac{c_0}{A} \sum_1 p_1^2 \quad \text{Eq. 4}$$

In order to apply Eq. 4 to the measurement of the radius bone mineral density, the unknown constant "$c_0$" shall be determined at first. In order to determine the constant "$c_0$", a large number of wrist x-ray images are obtained from different female subjects. After setting a region of interest for each wrist x-ray image, the first term $$<G> = \frac{1}{A} \sum_1 \sum_{n=b_1}^{c_1} G_{In}$$

and the second term $$P \equiv \frac{1}{A} \sum_1 p_1^2$$

in the right-hand side of Eq. 4 are calculated. The second term "P" can be replaced with a form of $$\sum_1 p_1 \cdot \left( p_1 \bigg/ \sum_k p_k \right).$$

Then "P" represents a weighted average of the radius bone widths within the region of interest described previously. Generally, the weighted average is not so different from a simple average, so the "P" can be chosen as a simple average of "$p_I$" within the region of interest, i.e. the average width of the radius bone within the region of interest.

Each female subject has undergone the bone mineral density (BMD) measurement within the same radius portion by using a DEXA equipment. Then, the constant $c_0$ is set to a value that minimizes the least-squares fit error between BMD and "$<G>+c_0P$". As for 200 female subjects, the constant $c_0$ set by the least-squares fit is 0.10.

Now, as the necessary constant $c_0$ is determined, the index for the radius bone mineral density is given by $<G>+c_0P$. Generally, the value $<G>$ is several times larger than the value $c_0P$, and the average subject-to-subject variation of the value P is about 4%. On the contrary, the average subject-to-subject variation of the value $<G>$ is about 40%. Accordingly, the index for the bone mineral density can be approximately set by only $<G>$.

As described in the concrete embodiment, the numbers or images used in the embodiment can be replaced with other ones to improve the performance of the method by the present invention. The key point of the present invention is to measure the bone mineral density by removing the x-ray absorption effect due to overlapping soft tissues in the bone image, on measuring the bone mineral density by using the x-ray images. The prior art to measure bone mineral density by using x-ray images didn't remove the x-ray absorption effect due to the overlapping soft tissues on the bone image, so there remained many possibilities of resulting in a lot of errors. However, in the present invention, a gray-level profile of the soft tissues surrounding the bone portion is interpolated into the bone portion. Then, in the bone region, the interpolated gray-level profile is removed from the gray-level profile of the bone portion. Furthermore, in the present invention, the method of modeling the cross-section of the bone to a disc shape is used to compensate for the error due to the size or shape variation of the bone.

The method of the present invention can be implemented by a program and stored in a computer-readable medium, e.g., a CD-ROM, a RAM, a floppy disk, a hard disk, an optical magnetic disk, etc.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A method for measuring a bone mineral density, by use of an x-ray image, in a bone mineral density measuring system, comprising the steps of:
    (a) obtaining an X-ray image of bone;
    (b) setting a region of interest on the obtained X-ray image of bone;
    (c) calculating a background trend due to soft tissues, at a bone portion within the set region of interest;
    (d) removing the background trend from a gray-level of each pixel at the bone portion;
    (e) calculating an average value ($<G>$) of gray-level values at the bone portion after the background trend is removed;
    (f) calculating a weighted average (P) of the bone widths within the region of interest; and
    (g) calculating an index of the bone mineral density by adding a value of the weighted average (P) multiplied by a specific constant ($c_0$) to the average value ($<G>$), at the bone portion within the set region of interest.

2. The method as recited in claim 1, wherein the region of interest, containing the soft tissue portions at a left and right of the bone portion, is set in the obtained x-ray image of bone.

3. The method as recited in claim 1, wherein said step (c) includes the steps of;
    (c1) selecting a fitting function to calculate the background trend of the bone portion; and
    (c2) setting the background trend by interpolating the gray-level profiles of the soft tissue portions adjacent to the bone portion into the bone portion by the selected fitting function.

4. The method as recited in claim 3, wherein said step (c2) includes the steps of;
    (c2-a) obtaining the gray-level profile from the region of interest;
    (c2-b) dividing the obtained gray-level profile into the bone portion and the soft tissue portions; and
    (c2-c) interpolating the gray-level profiles of the divided soft tissue portions into the bone portion by the fitting function and setting and interpolation result to the background trend due to the soft tissues.

5. The method as recited in claim 3, wherein the fitting function is a polynominal of a $4^{th}$ order or less.

6. The method as recited in claim 5, wherein a fitting of the polynomial is done by a Levenberg-Marquardt fitting method.

7. The method as recited in claim 1, wherein the weighted average (P) is set to the average bone width within the region of interest.

8. The method as recited in claim 1, wherein the weighted average (P) is set by dividing a sum of squares of the bone widths within the region of interest by a sum of the bone widths within the region of interest.

9. The method as recited in claim 1, wherein the specific constant ($c_0$) of said step (g) is set to zero.

10. The method as recited in claim 1, wherein the specific constant ($c_0$) of said step (g) is set to a value that minimizes a least-squares fit error between the index of bone mineral density ($<G>+c_0P$) and the bone mineral density measured by a bone mineral density measuring equipment.

11. A computer readable recording medium storing instructions to implement a method for measuring a bone mineral density, by use of an x-ray image, in a bone mineral density measuring system, said method comprising the steps of:
    (a) obtaining an X-ray image of bone;
    (b) setting a region of interest on the obtained X-ray image of bone;
    (c) calculating a background trend due to soft tissues, at a bone portion within the set region of interest;
    (d) removing the background trend from a gray-level of each pixel at the bone portion;
    (e) calculating an average value ($<G>$) of gray-level values at the bone portion after the background trend is removed;
    (f) calculating a weighted average (P) of the bone widths within the region of interest; and
    (g) calculating an index of the bone mineral density by adding a value of the weighted average (P) multiplied by a specific constant ($c_0$) to the average value ($<G>$), at the bone portion within the set region of interest.

12. The storage medium as recited in claim 11, wherein said step (c) includes the steps of:
    (c1) selecting a fitting function to calculate the background trend at the bone portion; and
    (c2) setting the background trend by interpolating the gray-level profile of the soft tissue portions adjacent to the bone portion into the bone portion by the selected fitting function.

* * * * *